United States Patent
Iwasaki et al.

(10) Patent No.: US 8,123,356 B2
(45) Date of Patent: Feb. 28, 2012

(54) AMPLITUDE OF ACCOMMODATION MEASURING APPARATUS

(75) Inventors: Tsuneto Iwasaki, Kitakyushu (JP); Akihiko Tawara, Fukuoka (JP)

(73) Assignees: University of Occupational and Environmental Health, Japan, Kitakyushu-shi, Fukuoka (JP); Nikon Vision Co., Ltd., Tokyo (JP)

(*) Notice: Subject to any disclaimer, the term of this patent is extended or adjusted under 35 U.S.C. 154(b) by 213 days.

(21) Appl. No.: 12/593,288

(22) PCT Filed: Apr. 9, 2008

(86) PCT No.: PCT/JP2008/057372
§ 371 (c)(1),
(2), (4) Date: Sep. 26, 2009

(87) PCT Pub. No.: WO2008/129991
PCT Pub. Date: Oct. 30, 2008

(65) Prior Publication Data
US 2010/0118272 A1      May 13, 2010

(30) Foreign Application Priority Data
Apr. 19, 2007   (JP) ................................. 2007-110377

(51) Int. Cl.
*A61B 3/02* (2006.01)

(52) U.S. Cl. ....................................................... 351/239
(58) Field of Classification Search ................. 351/169, 351/177, 205, 239, 246
See application file for complete search history.

(56) References Cited

U.S. PATENT DOCUMENTS
2001/0026350 A1   10/2001   Fujieda

FOREIGN PATENT DOCUMENTS
JP    11-070076      3/1999
JP    2001-275974 A  10/2001

OTHER PUBLICATIONS

Oguchi et al., "Ophthalmic Examination Handbook (Handbook of Ophthalmology Inspection Method)," fourth edition, pp. 65-66, Igaku Shoin (publisher), Jun. 1, 2005.

*Primary Examiner* — Ricky Mack
*Assistant Examiner* — Mahidere Sahle
(74) *Attorney, Agent, or Firm* — Miles & Stockbridge P.C.

(57) ABSTRACT

Shift lenses 20L, 20R are provided on optical axes that pass through LCDs 40L, 40R for displaying an image for focusing. The shift lenses 20L, 20R are moved along the optical axes by pressing a focus button provided on a case 10 in accordance with an instruction displayed on the LCDs 40L, 40R. An amplitude of accommodation is calculated on the basis of a position where the image starts blurring upon moving the shift lenses 20L, 20R from a far point side focus position, and a position where the image starts blurring upon moving the shift lenses 20L, 20R from a near point side focus position.

4 Claims, 4 Drawing Sheets

AMPLITUDE OF ACCOMMODATION MEASURING APPARATUS

TECHNICAL FIELD

The present invention relates to an amplitude of accommodation measuring apparatus.

BACKGROUND ART

There has been proposed an amplitude of accommodation measuring apparatus that is equipped with a far optotype as a fixation object for a distal position and a near optotype as a fixation object for a near position, and measures amplitude of accommodation expressed by difference in refractive power at a near point and a far point, in which the near point is defined by a position where an outline of the near optotype starts blurring upon moving the near optotype toward an eye from a focus position of the near optotype, and the far point is defined by a position where an outline of the far optotype starts blurring upon moving the far optotype away from an eye from a focus position of the far optotype (see "Handbook of Opthalmology Inspection Method" fourth edition, pages 65-66, edited by KOGUCHI, Yoshihisa, and three others, published by Igaku Shoin on Jun. 1, 2005).

In the amplitude of accommodation measuring apparatus, the far point is measured by using the far optotype, the near point is measured by using the near optotype, and the amplitude of accommodation is derived from calculating difference between these positions.

However, in the conventional amplitude of accommodation measuring apparatus, in order to measure the near point and the far point, the optotypes and an additional trial lens have to be exchanged, so that it takes time to measure the amplitude of accommodation to make the apparatus hard to be handled.

DISCLOSURE OF THE INVENTION

The present invention is made in view of the aforementioned problems, and has an object to provide an amplitude of accommodation measuring apparatus capable of easily measuring the amplitude of accommodation without exchanging optotypes.

In order to solve the problem, the present invention provides an amplitude of accommodation measuring apparatus comprising: a display member that displays an image for focusing at a far point side and a near point side; an optical system for observing the image displayed on the display member; a driving member that moves the optical system along an optical axis according to an instruction given from outside; and a control member that calculates the amplitude of accommodation on the basis of a position where the image starts blurring from a far point side focus position by moving the optical system to the far point side by means of the driving member, and a position where the image starts blurring from a near point side focus position by moving the optical system to the near point side by means of the driving member.

In the present invention, it is preferable that instruction from outside is carried out by a push button provided on a case that stores the display member, the optical system, the driving member and the control member, and the control member controls the driving member to move the optical system along the optical axis only while the push button is pressed.

In the present invention, it is preferable that the control member controls the driving member such that a moving speed of the optical system toward the far point side from a far point side focus position of the image to a position where the image starts blurring is less than a moving speed of the optical system toward the far point side from an initialize position to the far point side focus position of the image, and a moving speed of the optical system toward the near point side from a near point side focus position of the image to a position where the image starts blurring is less than a moving speed of the optical system toward the near point side from the initialize position to the near point side focus position of the image.

In the present invention, it is preferable that determination of each of the point where the image starts blurring from the far point side focus position, and the point where the image starts blurring from the near point side focus position is instructed by the push button to the control member.

In the present invention, it is preferable that the far point side focus position is instructed by the push button to the control member, and after the instruction the control member controls the driving member to lower the moving speed of the optical system from the far point side focus position to the far point side, and the near point side focus position is instructed by the push button to the control member, and after the instruction the control member controls the driving member to lower the moving speed of the optical system from the near point side focus position to the near point side.

The present invention makes it possible to easily measure the amplitude of accommodation without exchanging optotypes or additional trial lenses.

THE EMBODIMENT FOR CARRYING OUT THE INVENTION

An embodiment of the present invention is explained with reference to accompanying drawings.

Figure 1:
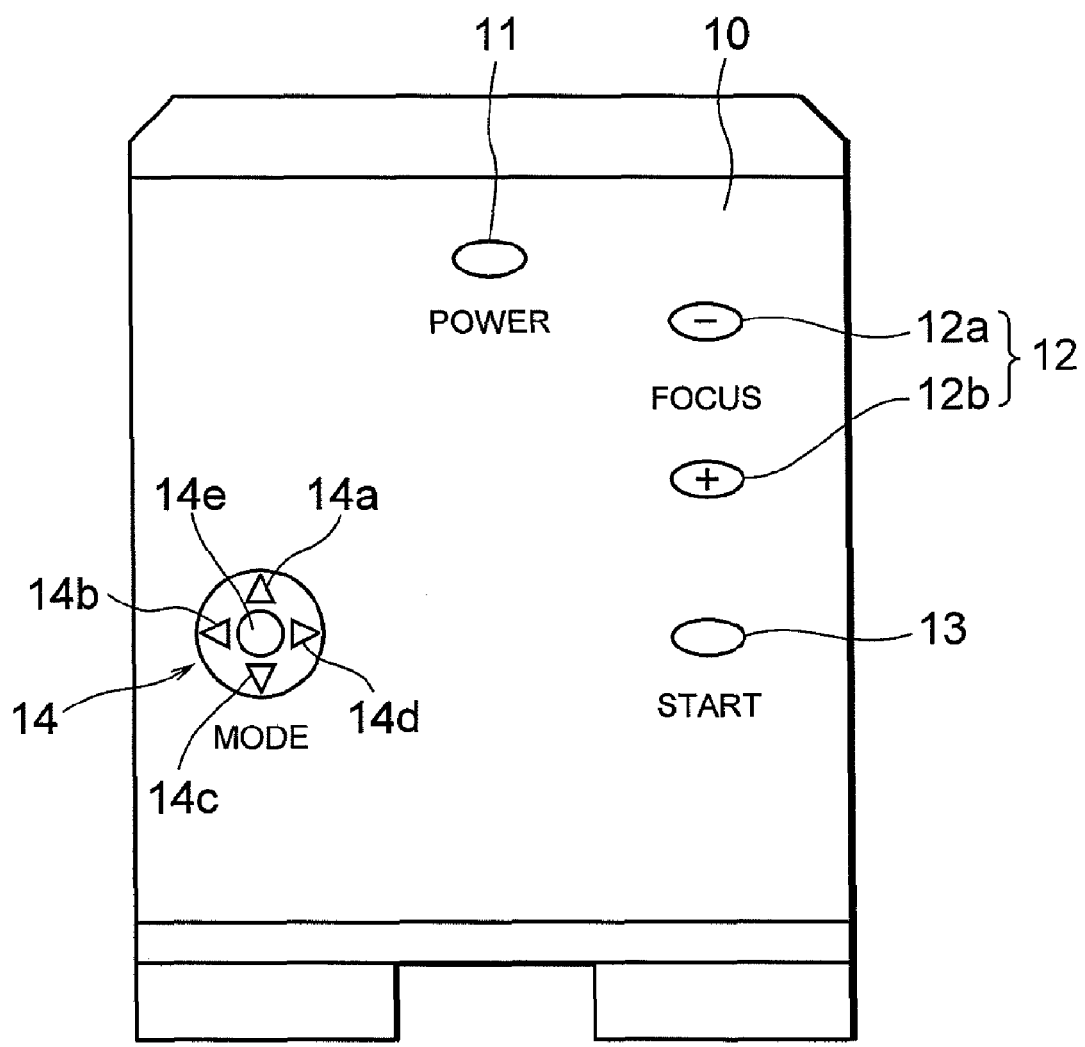
FIG. 1 is a plan view showing an amplitude of accommodation measuring apparatus according to an embodiment of the present invention.

FIG. 1 is a plan view showing an amplitude of accommodation measuring apparatus according to an embodiment of the present invention.

On an upper surface of a case 10 of the amplitude of accommodation measuring apparatus, there are provided a power button 11 (POWER), a focus button 12 (FOCUS), a start button 13 (START), and mode buttons 14 (MODE).

The power button 11 that is for switching the power of the amplitude of accommodation measuring apparatus on/off. When the power switch is on, images for focusing are displayed on LCDs (Liquid Crystal Displays) 40L, 40R (see FIG. 2).

The focus buttons 12 are for moving shift lenses 20L, 20R along optical axes L1, L2 of the shift lenses 20L, 20R, respectively. The focus buttons 12 have a push button 12a for moving the shift lenses 20L, 20R away from the eyes, and a push button 12b for moving the shift lenses 20L, 20R close to the eyes. Focusing is carried out by pushing the push buttons 12a, 12b.

The start button 13 is for instructing a CPU 51 (see FIG. 4) to calculate amplitude of accommodation.

Figure 2:
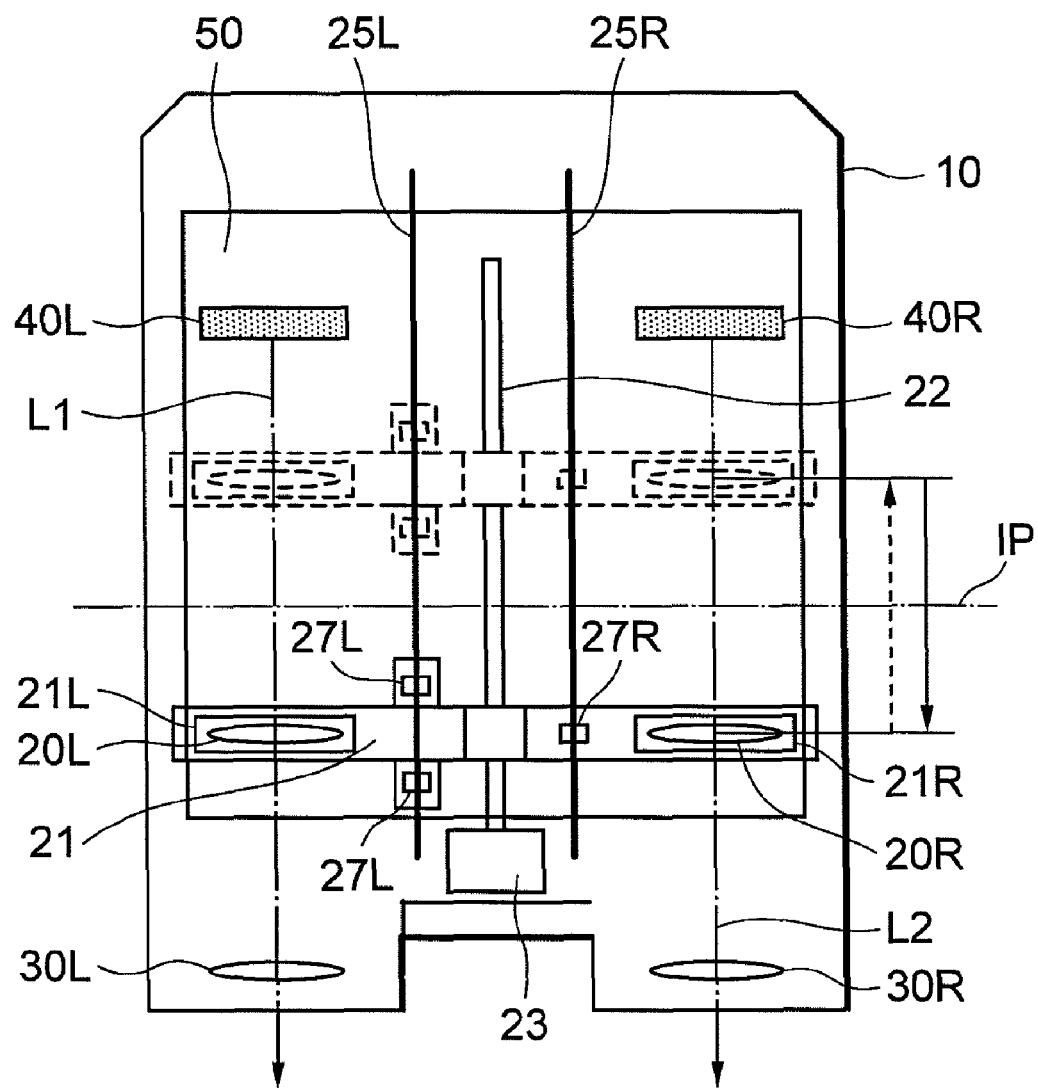
FIG. 2 is a schematic diagram showing a construction of the amplitude of accommodation measuring apparatus.

The mode button 14 is for selecting images displayed on the LCDs 40L, 40R (see FIG. 2). The mode button 14 has triangular selection keys 14a, 14b, 14c, and 14d, and a circular enter key 14e (ENTER). For example, when the enter key 14e is pressed after pressing the selection key 14b, an amplitude of accommodation measurement with a single eye is selected, and when the enter key 14e is pressed after pressing the selection key 14d, an amplitude of accommodation measurement with both eyes is selected. Moreover, when the enter key 14e is pressed after pressing the selection key 14a, the measurement is carried out one time, and when the enter key 14e is pressed after pressing the selection key 14c, the measurement is carried out a plurality of times. Moreover, when only the enter key 14e is pressed longer than a predetermined duration, the images displayed on the LCDs 40L, 40R are changed, and upon removing a finger from the enter key 14e, images at this moment are selected.

FIG. 2 is a schematic diagram showing a construction of the amplitude of accommodation measuring apparatus.

The amplitude of accommodation measuring apparatus is equipped with left and right shift lenses 20L, 20R for constructing an observation optical system, left and right dust proof glasses 30L, 30R, left and right LCDs 40L, 40R for composing a display member, and a control circuit 50 for composing a control member. The shift lenses 20L, 20R, dust proof glasses 30L, 30R, and LCD displays 40L, 40R, and control circuit 50 are installed in the case 10. The left LCD 40L and the left dust proof glass 30L are disposed on the optical axis L1 of the left shift lens 20L. The right LCD 40R and the right dust proof glass 30R are disposed on the optical axis L2 of the right shift lens 20R. The optical axis L1 and the optical axis L2 are parallel with each other. A user observes images displayed on the LCDs 40L, 40R from the dust proof glasses 30L, 30R through the shift lenses 20L, 20R. On the LCDs 40L, 40R, images for focusing or measurement results are displayed. When the power is off, the shift lenses 20L, 20R are located at initialize position IP that is the initial position.

The left shift lens 20L is installed in a left fix portion 21L. The right shift lens 20R is installed in a right fix portion 21R. The left fix portion 21L and the right fix portion 21R are fixed to a fixing portion 21.

Bearings 27L, 27R are provided on the fixing portion 21 between the left and right shift lenses 20L, 20R. Guide bars 25L, 25R are provided respectively to the bearings 27L, 27R movably relative to each other. The guide bars 25L, 25R extend along optical axes L1, L2 of the shift lenses 20L, 20R, respectively. The guide bars 25L, 25R are fixed to the case 10 by unillustrated fixing members. With this configuration, the fixing portion 21 is held by the guide bars 25L, 25R through the bearings 27L, 27R movably along the optical axes L1, L2. Accordingly, when the fixing portion 21 is moved along the optical axes L1, L2, the shift lenses 20L, 20R are moved along the optical axes L1, L2 in a body with the fixing portion 21.

At an intermediate position between the left and right shift lenses 20L and 20R, the fixing portion 21 is connected to a ball screw 22 that extends parallel to the optical axes L1, L2 and is connected to a stepping motor 23. The fixing portion 21 and the ball screw 22 are relatively movable along the optical axes L1, L2. A drive member is composed of the fixing portion 21, guide bars 25L, 25R, and the stepping motor 23. When the stepping motor 23 is rotated, the fixing portion 21 is moved along the optical axes L1, L2 in accordance with the rotation of the ball screw 22 connected to the stepping motor 23. The moving amount of the fixing portion 21 per one turn (360 degrees) of the ball screw 22 is fixed. Accordingly, by rotating the stepping motor 23 normally/reversely, the shift lenses 20L, 20R can be moved along the optical axes L1, L2 to a near point direction that is close to the eye as shown by solid arrow in FIG. 2 or to a far point that is away from the eye as shown by dotted arrow in FIG. 2 with the initialize position IP as the center.

In the stepping motor 23, since a rotation angle with respect to one pulse of the driving pulse is determined, with counting the number of pulses of the driving pulse of the stepping motor 23, the moving amount of the fixing portion 21 with respect to the ball screw can be detected. Accordingly, upon setting the initialize position IP of the shift lenses 20L, 20R as the origin, the position of the shift lenses 20L, 20R along the optical axes, for example, the focus position of the far point side or that of the near point side that is the focus position of the image for focusing displayed on the LCDs 40L, 40R at the far point side or the near point side can be detected with high accuracy.

The control circuit 50 calculates the amplitude of accommodation on the basis of a far point and a near point, in which the far point is a position where an image that is focused and is displayed on the LCDs 40L, 40R for focusing starts blurring by moving the shift lenses 20L, 20R from the far point side focus position, and the near point is a position where an image that is focused and is displayed on the LCDs 40L, 40R for focusing starts blurring by moving the shift lenses 20L, 20R from the near point side focus position. Moreover, the control circuit 50 controls a moving direction, a moving amount, a moving speed, and the like of the shift lenses 20L, 20R. For example, the control circuit 50 controls the stepping motor 23 such as moving the shift lenses 20L, 20R only when the focus button 12 is pressed, and controlling a moving speed of the shift lenses 20L, 20R from a position where the image for focusing is focused to a position where the image starts blurring is less than a moving speed of the shift lenses 20L, 20R from the initialize position IP to the focus position. This is effective for the user to precisely recognize a point where the image starts blurring.

In particular, instead of moving an optotype as is conventional apparatus, the present apparatus varies an optotype, in other words, the focus position of the image for focusing displayed on the LCDs 40L, 40R by moving the shift lenses 20L, 20R. In the conventional apparatus, since the moving amount of the optotype and the moving amount of the image of the optotype vary linearly, when refractive power of the eye of the user is varied linearly, the image of the optotype is always focused on the retina. However, in the present apparatus, the moving amount of the shift lenses 20L, 20R and the moving amount of the focusing position are not in linear relation, so that refractive power of the eye has to be varied non-linearly. Accordingly, at the position where the image for focusing starts blurring, it becomes important to precisely control the moving speed of the shift lens 20.

Figure 3:
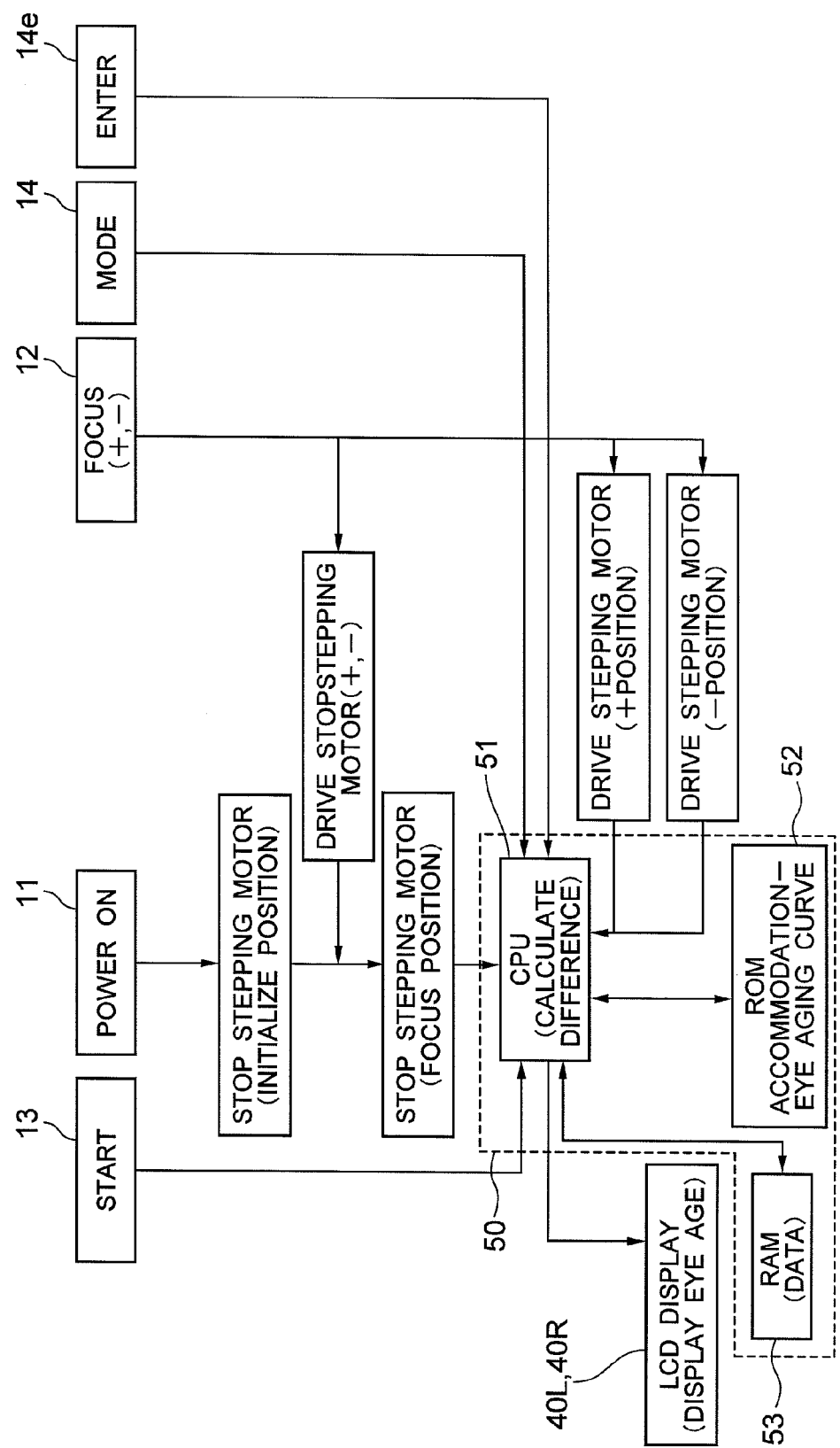
FIG. 3 is a block diagram explaining a using procedure of the amplitude of accommodation measuring apparatus.
Figure 4:
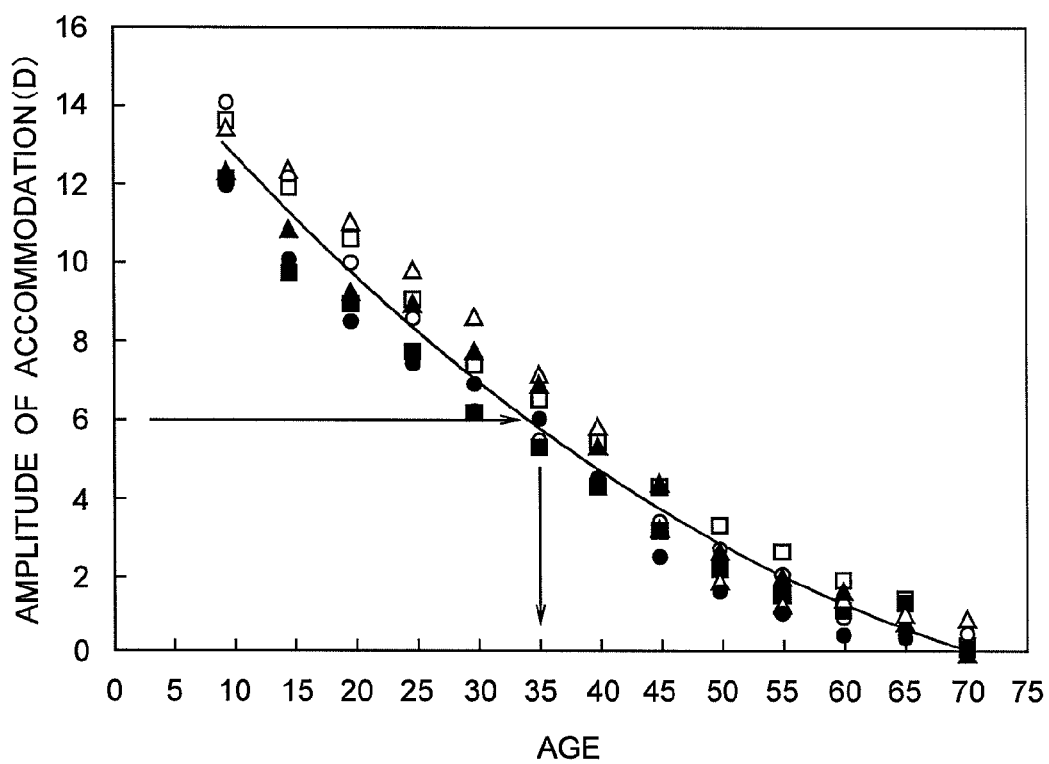
FIG. 4 is a graph showing amplitude of accommodation with respect to age.

FIG. 3 is a block diagram explaining a using procedure of the amplitude of accommodation measuring apparatus. FIG. 4 is a graph showing an amplitude of accommodation with respect to age. In FIG. 4, the vertical axis and the horizontal axis are the amplitude of accommodation (D) and the age, respectively.

In the control circuit 50, a CPU 51 is provided, and the CPU 51 is connected to a ROM 52 and a RAM 53 through a data bus. In the ROM 52, various control programs including the amplitude of accommodation curve of age shown in FIG. 4, measured result, in other words, the amplitude of accommodation, age derived from the amplitude of accommodation curve of age, and the amplitude of accommodation measuring program are stored. Incidentally, the contents of FIG. 4 is the same as that of FIG. 2 in page 66 of the above-described non-patent document. Data for calculation are stored in the RAM 53.

Then, how to use the amplitude of accommodation measuring apparatus is explained with reference to FIG. 3.

At first the power button 11 is pressed. Power is on, an image for focusing is displayed on the LCDs 40L, 40R. At this time, when the enter key 14e is pressed longer than a predetermined duration, the image can be changed. With watching the image, the push button 12a is pressed (see FIG. 1) according to the instruction displayed on the LCDs 40L, 40R, so that the shift lenses 20L, 20R are moved to a far point side focus position from the initialize position IP.

When the shift lenses 20L, 20R reach the far point side focus position, your finger is removed from the push button 12a, and the enter key 14e is pressed. Then, the push button 12a is pressed again to slightly move the shift lenses 20L, 20R in a direction away from the eyes. When the shift lenses 20L, 20R reach a position (− position) where the image starts blurring, the enter key 14e is pressed to determine the far point. The position is stored in the RAM 53 of the CPU 51 as a far point data. As described above, the moving speed of the shift lenses 20L, 20R after pressing the enter key 14e when the shift lenses have reached the far point side focus position is preferably made slower than that before pressing the enter key 14e.

Here, how to precisely and simply measure the amplitude of accommodation is explained.

The measuring method is: at first, measurement mode is changed to a second mode for measuring the amplitude of accommodation by the mode button 14; the shift lenses 20L, 20R are moved to the far point side or the near point side by means of the above-described operation or an operation described later; when the shift lenses 20L, 20R are reached the far point side focus position or the near point side focus position, and with displaying each focus-position-detecting mark at each focus position, a position where the image starts blurring is input. After completion of a series of inputs, measurement of the amplitude of accommodation is carried out. The following is a detailed explanation of the method.

At first, measurement mode is changed to a second mode for measuring the amplitude of accommodation by the mode button 14. Then, an operation method for inputting the far point side and the near point side focus positions are displayed on the LCDs 40L, 40R for a user. When the user inputs the far point side focus position according to the display, the shift lenses 20L, 20R move from the initialize position IP to the far point side. At this time, for example, a focus-position-detection-mark (hereinafter called a "position-detection mark") is displayed upper left corner of the LCDs 40L, 40R, the position-detection mark blinks while the shift lenses 20L, 20R move from the initialize position IP to the far point side focus position, upon reaching the far point side focus position, the position-detection mark is changed from blinking display to switch-on display. Accordingly, the user is notified that the shift lenses 20L, 20R reach the far point side focus position, and based on the switch-on display, the user presses the enter key 14e at the position where the image starts blurring. Regarding the near point side, the similar operation is to be carried out. With this operation, it becomes possible to objectively recognize the focus position, and a position where the image starts blurring is confirmed and input from the focus position, so that labors of the user can be lightened, and precise measurement can be carried out. This is the more precise and simple measurement method for the amplitude of accommodation.

Then, operation procedures after determining the far point are explained. After determining the far point, the push button 12b is pressed (see FIG. 1) with observing the image in accordance with an instruction displayed on the LCDs 40L, 40R to move the shift lenses 20L, 20R from initialize position IP to the near point side focus position.

When the shift lenses 20L, 20R reach the near point side focus position, the finger is removed from the push button 12b, and the enter key 14e is pressed. The push button 12b is pressed again to slightly move the shift lenses 20L, 20R in a direction close to the eye. In this instance, the moving speed of the shift lenses 20L, 20R after pressing the enter key 14e is preferably made slower than that before pressing the enter key 14e. When the shift lenses 20L, 20R reach a position (+ position) where the image starts blurring, the enter key 14e is pressed to determine the near point. The position is stored in the RAM 53 of the CPU 51 as a near point data.

Then, the start button 13 is pressed. On the basis of stored data in the ROM 52, the CPU 51 calculates difference between the far point and the near point that is the measured amplitude of accommodation.

The CPU 51 derives age referring from the amplitude of accommodation with respect to age curve stored as a default value in the ROM 52, and displays it together with the amplitude of accommodation on the LCDs 40L, 40R.

In this embodiment, the amplitude of accommodation can be obtained by simply pressing the focus button 12 and the like according to instructions displayed on the LCDs 40L, 40R, so that it does not take time to change the optotype for the far point, the optotype for the near point, and additional trial lenses as is conventional case. Since the shift lenses 20L, 20R move only while the focus button 12 is pressed, the focus position can easily be found. Moreover, moving speed of the shift lenses 20L, 20R from the focus position to a position where the image starts blurring is made slower than the moving speed of the shift lenses 20L, 20R from the initialize position IP to the focus position, so that the far point or the near point where the image starts blurring can easily be detected. Since the present embodiment does not need two changeable optotypes or additional trial lenses as the conventional case, it becomes possible to make it compact. Furthermore, since the shift lenses 20L, 20R, and the LCDs 40L, 40R are stored in the case 10, it is not affected by disturbing light, so that the image of the LCDs 40L, 40R can easily be observed to be easy to determine the amplitude of accommodation. Moreover, since the stepping motor 23 is adopted, measurement of the amplitude of accommodation can be carried out with high precision, and age of the eye can be derived precisely.

In the above-described embodiment, although a mode for measuring the amplitude of accommodation by both eyes is selected, a mode for measuring the amplitude of accommodation by a single eye can be selected by pressing the selection key 14b to be off one side of LCD (for example, LCD display 40L).

Moreover, in the above-described embodiment, although a mode for calculating the amplitude of accommodation only once by measuring the far point and the near point is selected, a mode for measuring the far point and the near point a plurality of times, and calculating the amplitude of accommodation can be selected by pressing the selection key 14c. When this mode is selected, the maximum value and the minimum value among the measured values of the far point and the near point carried out a plurality of times are cut off, and the amplitude of accommodation is calculated from the remained values, and the average value thereof is made to be the amplitude of accommodation, or average of the remained values is calculated, and from this value the amplitude of accommodation is calculated to be displayed on the LCDs 40L, 40R.

Furthermore, in the above-described embodiment, although the shift lenses 20L, 20R are moved along the optical axes, instead of this, the LCDs 40L, 40R may be moved along the optical axes.

In the above-described embodiment, although two LCDs 40L, 40R are disposed, only one LCD display may be disposed. In this case, a plurality of mirrors and shutters for leading the image to the left and right shift lenses 20L, 20R are disposed on the optical path.

What is claimed is:

1. An amplitude of accommodation measuring apparatus comprising:
    a display member that displays an image for focusing at a far point side and a near point side;
    an optical system for observing the image displayed on the display member;
    a driving member that moves the optical system along an optical axis according to an instruction given from outside; and
    a control member that calculates the amplitude of accommodation on the basis of a position where the image starts blurring from a far point side focus position by moving the optical system to the far point side by means of the driving member, and a position where the image starts blurring from a near point side focus position by moving the optical system to the near point side by means of the driving member, and controls the driving member such that a moving speed of the optical system toward the far point side from a far point side focus position of the image to a position where the image starts blurring is less than a moving speed of the optical system toward the far point side from an initialize position to the far point side focus position of the image, and
    a moving speed of the optical system toward the near point side from a near point side focus position of the image to a position where the image starts blurring is less than a moving speed of the optical system toward the near point side from the initialize position to the near point side focus position of the image.

2. The amplitude of accommodation measuring apparatus according to claim 1, wherein instruction from outside is carried out by a push button provided on a case that stores the display member, the optical system, the driving member and the control member, and the control member controls the driving member to move the optical system along the optical axis only while the push button is pressed.

3. The amplitude of accommodation measuring apparatus according to claim 2, wherein determination of each of the point where the image starts blurring from the far point side focus position, and the point where the image starts blurring from the near point side focus position is instructed by the push button to the control member.

4. The amplitude of accommodation measuring apparatus according to claim 1, wherein
    the far point side focus position is instructed by the push button to the control member, and after the instruction the control member controls the driving member to lower the moving speed of the optical system from the far point side focus position to the far point side, and
    the near point side focus position is instructed by the push button to the control member, and after the instruction the control member controls the driving member to lower the moving speed of the optical system from the near point side focus position to the near point side.

* * * * *